(12) United States Patent
Sawhney

(10) Patent No.: US 6,818,018 B1
(45) Date of Patent: *Nov. 16, 2004

(54) IN SITU POLYMERIZABLE HYDROGELS

(75) Inventor: Amarpreet S. Sawhney, Bedford, MA (US)

(73) Assignee: Incept LLC, Lexington, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/133,940

(22) Filed: Aug. 14, 1998

(51) Int. Cl.$^7$ .................................................. A61F 2/02
(52) U.S. Cl. ................................ 623/11.11; 623/23.58; 623/926; 523/113
(58) Field of Search ..................... 623/11, 16, 11.11, 623/16.11, 23.58, 23.59, 23.61, 924, 926; 523/113, 115

(56) References Cited

U.S. PATENT DOCUMENTS

| | | |
|---|---|---|
| 3,833,003 A | 9/1974 | Taricco .......................... 128/347 |
| 3,949,073 A | 4/1976 | Daniels et al. ................. 424/177 |
| 3,991,766 A | 11/1976 | Schmitt et al. ............. 128/335.5 |
| 4,101,380 A | 7/1978 | Rubinstein et al. ............. 195/63 |
| 4,107,121 A * | 8/1978 | Stoy ............................. 260/29.6 |
| 4,141,973 A | 2/1979 | Balazs ........................... 424/180 |
| 4,195,129 A | 3/1980 | Fukui et al. .................. 435/182 |
| 4,507,466 A | 3/1985 | Tomalia et al. ............... 528/332 |
| 4,511,478 A | 4/1985 | Nowinski et al. ............ 210/691 |
| 4,532,134 A | 7/1985 | Malette et al. ................. 514/21 |
| 4,568,737 A | 2/1986 | Tomalia et al. ............... 528/332 |
| 4,717,378 A * | 1/1988 | Perrault et al. ................ 604/20 |
| 4,740,534 A | 4/1988 | Matsuda et al. .............. 523/111 |
| 4,804,691 A | 2/1989 | English et al. ............... 523/118 |
| 4,839,345 A | 6/1989 | Doi et al. ........................ 514/21 |
| 4,886,787 A | 12/1989 | deBelder et al. ............... 514/57 |
| 4,911,926 A | 3/1990 | Henry et al. .................. 424/426 |
| 4,979,959 A | 12/1990 | Guire ............................. 623/66 |
| 4,994,277 A | 2/1991 | Higham et al. ................ 424/443 |
| 5,093,319 A | 3/1992 | Higham et al. ................. 514/55 |
| 5,122,614 A | 6/1992 | Zalipsky ........................ 548/520 |
| 5,126,141 A | 6/1992 | Henry ........................... 424/423 |
| 5,140,016 A | 8/1992 | Goldberg et al. ............... 514/57 |
| 5,152,782 A | 10/1992 | Kowligi et al. .................. 623/1 |
| 5,171,148 A | 12/1992 | Wasserman et al. .......... 433/215 |
| 5,190,759 A | 3/1993 | Lindblad et al. .............. 424/423 |
| 5,198,220 A | 3/1993 | Damani ........................ 424/426 |
| 5,213,580 A | 5/1993 | Slepian et al. ................... 623/1 |
| 5,246,698 A | 9/1993 | Leshchiner et al. ........ 424/78.08 |
| 5,266,326 A | 11/1993 | Barry et al. ................... 424/423 |
| 5,304,147 A | 4/1994 | Johnson et al. ................ 604/20 |
| 5,328,939 A * | 7/1994 | Smith ............................ 521/187 |
| 5,366,498 A | 11/1994 | Brannan et al. ................ 623/11 |
| 5,385,561 A | 1/1995 | Cerny ............................ 604/264 |
| 5,410,016 A | 4/1995 | Hubbell et al. ............... 528/354 |
| 5,462,976 A | 10/1995 | Matsuda et al. ................ 522/74 |
| 5,462,990 A | 10/1995 | Hubbell et al. | 
| 5,509,899 A | 4/1996 | Fan et al. ........................ 604/96 |
| 5,514,379 A | 5/1996 | Weissleder et al. |
| 5,529,914 A | 6/1996 | Hubbell et al. .............. 435/182 |
| 5,573,934 A | 11/1996 | Hubbell et al. .............. 435/177 |
| 5,580,923 A | 12/1996 | Yeung et al. |
| 5,583,114 A | 12/1996 | Barrows et al. ................ 514/21 |
| 5,588,960 A | 12/1996 | Edwards et al. ............... 604/20 |
| 5,599,552 A | 2/1997 | Dunn et al. |
| 5,605,938 A | 2/1997 | Roufa et al. ................... 514/59 |
| 5,612,050 A | 3/1997 | Rowe et al. .................. 424/423 |
| 5,624,840 A | 4/1997 | Naughton et al. ........... 435/395 |
| 5,626,863 A | 5/1997 | Hubbell et al. .............. 424/426 |
| 5,660,849 A | 8/1997 | Polson et al. |
| 5,665,063 A | 9/1997 | Roth et al. ..................... 604/53 |
| 5,665,477 A | 9/1997 | Meathrel et al. |
| 5,688,855 A | 11/1997 | Stoy et al. |
| 5,744,545 A | 4/1998 | Rhee et al. |
| 5,752,974 A | 5/1998 | Rhee et al. |
| 5,820,918 A * | 10/1998 | Ronan et al. ................ 623/924 |
| 5,863,551 A | 1/1999 | Woerly |
| 5,874,500 A | 2/1999 | Rhee et al. |
| 5,990,194 A * | 11/1999 | Dunn et al. .................. 523/113 |
| 6,005,020 A * | 12/1999 | Loomis ....................... 523/105 |
| 6,051,648 A * | 4/2000 | Rhee et al. ................. 525/54.1 |
| 6,060,534 A * | 5/2000 | Ronan et al. ................ 523/113 |
| 6,113,629 A * | 9/2000 | Ken ............................. 623/1.1 |
| 6,162,241 A | 12/2000 | Coury et al. |
| 6,201,065 B1 | 3/2001 | Pathak et al. |

FOREIGN PATENT DOCUMENTS

| | | | |
|---|---|---|---|
| WO | WO 90/13540 | 11/1990 | ......... C07D/207/46 |
| WO | WO 94/25080 | 11/1994 | ........... A61L/27/00 |
| WO | WO 97/19973 | 6/1997 | |
| WO | WO 97/22371 | 6/1997 | ........... A61L/27/00 |
| WO | WO 99/08718 | 2/1999 | |

OTHER PUBLICATIONS

Morrison and Boyd, Organic Chemistry, Third Edition, (1973), pp. 27–28.*

Nagaoka, S. et al., "Interaction Between Blood Components and Hydrogels with Poly(oxyethylene) Chains," *Polymers As Biomaterials*, Shalaby, S.W. et al., eds., Plenum Press, New York, 361–374 (1984).

(List continued on next page.)

*Primary Examiner*—Paul Prebilic
(74) *Attorney, Agent, or Firm*—Patterson, Thuente, Skaar & Christensen, P.A.

(57) ABSTRACT

Compositions and methods for forming hydrogels in situ through a combination of physical and chemical crosslinking processes are provided in which physical crosslinking is mediated by one or more natural or synthetic components that stabilize the a hydrogel-forming precursor solutions at a deposition site for a period of time sufficient for more resilient chemical crosslinks to form. Methods of using such hydrogels as tissue coatings to prevent postsurgical adhesion formation, as tissue augmentation or luminal occlusion aids, as matrices for carrying cells, drugs or other bioactive species, as tissue sealants or adhesives, and as medical device coatings also are provided.

32 Claims, No Drawings

OTHER PUBLICATIONS

Park, K., "Enzyme–Digestible Swelling Hydrogels as Platforms for Long–Term Oral Drug Delivery: Synthesis and Characterization," *Biomaterials*, 9:435–441 (1988).

Park, K. et al., *Biodegradable Hydrogels for Drug Delivery*, Technomic Publishing Co., Inc., Lancaster, Pennsylvania (1993).

*Remington's Pharamceutical Sciences*, 14th Ed., J.E. Hoover et al., eds., Mack Publishing Co., Easton, Pennsylvania (1970).

Sawhney, A.S. et al., "Bioerodible Hydrogels Based on Photopolymerized Poly(ethylene glycol)–co–poly(α–hydroxy acid) Diarylate Macromers," *Macromolecules*, 26:581–587 (1993).

Shalaby, S.W., "Bioabsorbable Polymers," *Encyclopedia of Pharmaceutical Technology*, Swarbrick, J. et al., eds., Marcel Dekker, Inc., New York, 1:465–476 (1988).

Shalaby, S.W. et al., "In Vitro and In Vivo Studies of Enzyme–Digestible Hydrogels for Oral Drug Delivery," *J. Controlled Release*, 19:131–144 (1992).

Silberberg, A., "Network Deformation in Flow," *Molecular Basis of Polymer Networks*, Baumgartner, A. et al., eds., Springer–Verlag, Berlin, 42:147–151 (1989).

Smith, K.L. et al., "Association Reactions for Poly(alkylene Oxides) and Polymeric Poly (carboxylic Acids)," *Ind. Eng. Chem.*, 51(11):1361–1364 (1959).

*The Drug, The Nurse, The Patient (Including Current Drug Handbook)*, Falconer's 7th Ed., W.B. Saunders Co., Philadelphia, Pennsylvania (1974).

Zalipsky, S. et al., "Esterification of Polyethylene Glycols," *J. Macromol. Sci.–Chem.*, A21(6&7):839–845 (1984).

Abuchowski, A. et al., "Cancer Therapy with Chemically Modified Enzymes. I. Antitumor Properties of Polyethylene Glycol–Asparaginase Conjugates," *Cancer Biochem. Biophys.*, 7:175–186 (1984).

Bhatia, S. et al., "The Effect of Site of Implantation and Animal Age on Properties of Polydioxanone Pins," *J. Biomater. Sci. Polymer. Edn.*, Bamford, C.H. et al., eds., 6(5):435–446 (1994).

Boyers, S.P. et al., "Reduction of Postoperative Pelvic Adhesions in the Rabbit with Gore–Tex* Surgical Membrane," *Fertility and Sterility*, 49(6):1066–1070 (1988).

Chung, R.P.–T. et al., "Recent Developments in Free–Radical Polymerization—A Mini Review," *Progress in Organic Coatings*, Funke, W. et al., eds., 21(4):227–254 (1992).

Holtz, G., "Prevention and Managment of Peritoneal Adhesions," *Fertility and Sterility*, 41(4):497–507 (1984).

Jarrett P.K. et al., "Bioabsorbable Hydrogel Tissue Barrier: In Situ Gelation Kinetics," *Trans. Soc. Biomater.*, vol. XVIII: 182 (1995).

*Medicinal Chemistry*, 3rd Ed., Parts 1 and 2, Burger, A., ed., Wiley–Interscience.

* cited by examiner

IN SITU POLYMERIZABLE HYDROGELS

FIELD OF THE INVENTION

The present invention relates generally to the in situ formation of hydrogels, and more specifically, to compositions of hydrogels that are formed in situ by a combination of physical and chemical crosslinking.

BACKGROUND OF THE INVENTION

Hydrogels are materials which absorb solvents (such as water), undergo rapid swelling without discernible dissolution, and maintain three-dimensional networks capable of reversible deformation. Hydrogels have been proposed for use in a number of medical applications, including barriers to prevent post-surgical adhesion, as tissue adhesives, as bone implants, and for occluding naturally-occurring and iatrogenically formed lumens.

Hydrogels may be either uncrosslinked or crosslinked. Crosslink formation in polymers is usually accompanied by an increase in viscosity due to an increase in apparent or real molecular weight, and often may result in the formation of a gelled state.

Polymers may be crosslinked by either physical or chemical means. Physical crosslinking differs from chemical crosslinking in that the linkages are typically weaker, of lower energy, and often reversible. Thus, physically crosslinked hydrogels often are deformable mechanically. Four fundamental forces have been found to be responsible for producing physical crosslinking: ionic interactions; hydrophobic interactions; hydrogen bonding and Van der Waals forces.

Gel forming compositions for use in preventing post-surgical adhesion are known. For example, U.S. Pat. No. 4,994,277 to Higham et al. describes a barrier to prevent post-surgical adhesions formed from a water soluble xanthan gum gel. The water solubility of the gel may lead to inadequate retention duration, and risk of displacement and migration.

U.S. Pat. No. 4,911,926 to Henry et al. describes methods and composition for reducing post-surgical adhesions by using aqueous and non-aqueous compositions comprising polyoxyalkylene block copolymers that form gels in the biologic environment.

The hydrogels described in the foregoing patent form weak physical crosslinks that give the gels a paste-like consistency at physiological temperatures. Because the resulting gels are not covalently crosslinked, however, they have no mechanical integrity and may be readily displaced from the application site.

U.S. Pat. No. 5,126,141 to Henry describes compositions and methods for reducing post-surgical adhesions with thermo-irreversible gels of polyoxyalkylene polymers and ionic polysaccharides. Both the polyoxyalkylene and ionic polysaccharide are crosslinked by physical crosslinks; no covalent crosslinking is disclosed.

Other gel forming compositions for use in preventing post-surgical adhesion have included: (a) chitin derivatives (U.S. Pat. No. 5,093,319) (b) chitosan-coagulum (U.S. Pat. No. 4,532,134); and (c) hyaluronic acid (U.S. Pat. No. 4,141,973). There is no clear mechanism for degrading these tonically crosslinked materials, or their constituent molecules, which may remain within the body for uncertain periods of time.

Likewise, U.S. Pat. No. 5,266,326 to Barry et al. describes in situ modification of alginate to form a hydrogel spinal implant in vivo. Ionically crosslinked polysaccharides such as alginate are not absorbable in humans since no enzyme exists in humans to degrade the $\beta$ glycosidic linkages. Also, the high molecular weight of the alginates used (upwards of 200,000 Da) does not allow filtration through the kidneys.

Covalently crosslinked hydrogels have been prepared based on crosslinked polymeric chains of methoxy poly (ethylene glycol) monomethacrylate having variable lengths of the polyoxyethylene side chains. The interaction of these hydrogels with blood components is reported in Nagaoka, et al., in *Polymers as Biomaterial* (Shalaby et al., Eds.) Plenum Press, 1983, p. 381.

U.S. Pat. No. 5,573,934 to Hubbell et al. describes ethylenically unsaturated water soluble macromers that can be crosslinked in contact with tissues, cells, and bioactive molecules to form gels. The patent does not describe the inclusion of physically crosslinkable components to facilitate in situ formation of hydrogels.

U.S. Pat. No. 4,740,534 to Matsuda et al. describes surgical adhesives comprising urethane prepolymers used in combination with an unsaturated cyano compound containing a cyano group attached to a carbon atom, such as cyano(meth)acrylic acids and esters thereof.

U.S. Pat. No. 4,804,691 to English et al. describes a method of making an adhesive that is polymerized in situ to join soft living tissue, including steps of preparing a hydroxyl-terminated polyester by reacting a biodegradable monomer with a polyhydroxy polymerization initiator. When applied to the moist soft tissue, the adhesive reacts with water to yield a cured adhesive having a resorbable backbone with urethane linkages. The adhesive is not water soluble, however, and thus cannot intimately mix with tissue fluids. Also, because the adhesive reacts with water, it cannot be applied as an aqueous solution or suspension, and has poor adherence in the presence of excess surface moisture on tissue.

U.S. Pat. No. 5,462,976 to Matsuda et al. describes in situ polymerizable tissue barriers formed from photocurable glycosaminoglycan derivatives that are water soluble in their precursor form. These materials require external energy sources for transformation and polymerize slowly. U.S. Pat. No. 5,410,016 to Hubbell et al. describes biodegradable hydrogels that polymerize more rapidly by a photoinitiated free radical polymerization from water soluble macromers.

Synthesis and biomedical and pharmaceutical applications of absorbable or biodegradable hydrogels based on covalently crosslinked networks comprising polypeptide or polyester components as the enzymatically or hydrolytically labile components, respectively, have been described by a number of researchers. See, e.g., Jarrett, et al., "Bioabsorbable Hydrogel Tissue Barrier: In Situ Gelation Kinetics", *Trans. Soc. Biomater.*, Vol. XVIII, 182 (1995); Sawhney et al., "Bioerodible Hydrogels Based on Photopolymerized Poly(ethyleneglycol)-copoly($\alpha$-hydroxy acid) Diacrylate Macromers", Macromolecules, 26:581-587 (1993); Park, et al., *Biodegradable Hydrogels for Drua Delivery*, Technomic Pub., Lancaster, Pa., 1993; Park, "Enzyme-digestible Swelling Hydrogels as Platforms for Long-term Oral Drug Delivery: Synthesis and Characterization", Biomaterials, 9:435 (1988). None of these references suggest the desirability of providing physical crosslinking in addition to chemical crosslinking to improve hydrogel formation in situ.

Several previously known chemical systems are compatible with carrying out chemical reactions or crosslinking in vivo to form covalently crosslinked hydrogels. Monomers or macromers usable to form hydrogels by chemical crosslinking may be viewed as comprising two broad categories, depending on the kind of functional groups that are active in the crosslinking process. When these functional groups are self condensible, as is the case for example for ethylenically unsaturated functional groups, the crosslinker is by itself sufficient to result in the formation of a hydrogel, when polymerization is initiated with appropriate agents. In situ polymerized hydrogels also can be formed by crosslinking reactions that are a result of a reaction between dissimilar functional groups that have a tendency to react under physiological conditions in timeframes relevant for in situ polymerization.

U.S. Pat. No. 5,122,614 to Zalipsky describes that PEG molecules activated with an oxycarbonyl-N-dicarboximide functional group can be attached under aqueous, basic conditions by a urethane linkage to the amine group of a polypeptide. Activated PEG-N-succinimide carbonate is said to form stable, hydrolysis-resistant urethane linkages with amine groups. The amine group is shown to be more reactive at basic pHs of from about 8.0 to 9.5, and reactivity falls off sharply at lower pH.

The foregoing patent to Zaplinsky also describes several other previously known PEG derivatives. PEG-succinoyl-N-hydroxysuccinimide ester is said to form ester linkages having limited stability in aqueous media, thus indicating an undesirable short half-life. PEG-cyanuric chloride is said to exhibit an undesirable toxicity and to be non-specific for reaction with particular functional groups on a protein. PEG-phenylcarbonate is said to produce toxic hydrophobic phenol residues that have affinity for proteins. PEG activated with carbonyldiimidazole is said to be too slow in reacting with protein functional groups, requiring long reaction times to obtain sufficient modification of the protein.

Still other PEG derivatives have been proposed for attachment to functional groups on amino acids other than the epsilon $—NH_2$ of lysine. Histidine contains a reactive imino moiety, represented structurally as —N(—H)—, but many derivatives that react with epsilon $—NH_2$ also react with —N(—H)—. Cysteine contains a reactive thiol moiety, represented structurally as —SH, but the PEG derivative maleimide that is reactive with this moiety is subject to hydrolysis.

Considerable effort regarding previously known compositions has gone into developing various PEG derivatives for attachment to, in particular, the $—NH_2$ moiety on the lysine amino acid fraction of various proteins. Many of these derivatives have proven problematic in their synthesis and use. Some form unstable linkages with the protein that are subject to hydrolysis and therefore do not last very long in aqueous environments, such as in the blood stream. Some form more stable linkages, but are subject to hydrolysis before the linkage is formed, which means that the reactive group on the PEG derivative may be inactivated before the protein is attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. However, in all of the foregoing cases, the object of the modification was to form a soluble product, not a crosslinked hydrogel.

U.S. Pat. No. 5,583,114 to Barrows et al. describes an adhesive composition formed from a two component mixture including a first part comprising a serum albumin protein in an aqueous buffer having a pH in a range of about 8.0–11.0, and a second part comprising a water-compatible or water-soluble bifunctional crosslinking agent. Several minutes are needed for these materials to polymerize and only serum albumin is appropriate for reacting with bifunctional crosslinking agents. The crosslinking agents described in the Barrows patent are only PEG based and are also relatively slow acting.

International Publication WO 97/22371 to Rhee et al. describes the use of a hydrogel composition that is produced by the reaction of a synthetic nucleophilic polymer containing two or more nucleophilic groups with a second synthetic polymer containing two or more electrophilic groups. The compositions described in the patent take from 5 to 50 minutes to achieve crosslinking. Moreover, electrophilic functional groups that are expected to be more reactive are also reactive with the hydroxyl groups of water and thus have very limited stability at physiological pHs. Accordingly, the compositions described in that reference are unsuitable for tissue sealing and/or coating type applications, because it would be difficult to retain the hydrogels at the application site for the extended periods of time required for reactions to take place with shelf stable compositions.

In view of the foregoing, it would be desirable to provide methods and compositions for forming a hydrogel implant in situ by a combination of physical and chemical crosslinking of solutions of substantially water soluble precursors, wherein the physical crosslinking assists in retaining the hydrogel in place at a deposition site while the more durable chemical crosslinks are formed.

It further would be desirable to provide methods and compositions that result in the formation of absorbable or non-absorbable hydrogels by appropriate structural design of the hydrogel forming precursors.

It still further would be desirable to provide physically and chemically crosslinked hydrogels systems suitable for use in medical applications, such as reducing post-surgical tissue adhesion, plugging lumens, sealing tissue, gluing tissues together, and supporting or augmenting tissue either from within the tissue matrix, over the tissue surface, or as an adjunct with another supporting biomaterial.

It also would be desirable to provide methods and compositions for controlled and local, regional or systemic drug delivery.

SUMMARY OF THE INVENTION

In view of the foregoing, it is an object of the present invention to provide methods and compositions for forming a hydrogel implant in situ by a combination of physical and chemical crosslinking of solutions of substantially water soluble precursors.

It is also an object of the present invention to provide methods and compositions that result in the formation of absorbable or non-absorbable hydrogels by appropriate structural design of the hydrogel forming precursors.

It is another object of this invention to provide methods of using the hydrogels of the present invention to reduce post-surgical tissue adhesion, plug lumens, seal tissue, glue tissues together and support or augment tissue either from within the tissue matrix, over the tissue surface, or as an adjunct with another supporting biomaterial.

It is a further object of this invention to provide methods and compositions for controlled and local, regional or systemic drug delivery.

These and other objects of the invention are accomplished by providing compositions forming hydrogels in situ through a combination of physical and chemical crosslinking processes. Preferably, the hydrogel precursor components are all selected to be "substantially water soluble," having a solubility of at least 1 mg/L in an aqueous solution or in a mix of one or more water miscible solvents compatible for use in a physiological environment.

Physical crosslinking is mediated by one or more natural or synthetic components that act individually or synergistically to stabilize the hydrogel-forming precursor solution at a deposition site for a period of time sufficient for more resilient chemical crosslinks to form. The physical crosslinks may result from complexation, hydrogen bonding, desolvation, Van der Waals interactions, ionic bonding, etc., and may be initiated by mixing two components that are physically separated until combined in situ, or as a consequence of a prevalent condition in the physiological environment, such as temperature, pH, ionic strength, etc.

Chemical crosslinking is mediated by a single or multiple precursor components that form a covalently crosslinked network, thereby providing physical integrity and permanence (or absorbability) to the hydrogel implant. If the hydrogel is to be bioabsorbable, the polymerizable precursor components preferably include at least one linkage susceptible to cleavage, either by hydrolysis, by thermal degradation, or by other physiological processes including enzymatic or cellular activity. The chemical crosslinking may be accomplished by any of a number of mechanisms, including free radical polymerization, condensation polymerization, anionic or cationic polymerization, step growth polymerization, etc.

Methods of using the hydrogels of the present invention as tissue coatings to prevent postsurgical adhesion formation, as tissue augmentation or luminal occlusion aids, as matrices for carrying cells, drugs or other bioactive species, as tissue sealants or adhesives, and as medical device coatings are also provided.

DETAILED DESCRIPTION OF THE INVENTION

This written description includes the following sections: compositions prepared in accordance with the principles of the present invention are described together with suitable components. Medical applications for the compositions of the present invention are provided along with suitable delivery systems and bioactive species. Illustrative example compositions and medical applications are then presented.

In situ formed hydrogels are known for use in numerous medical applications, where the hydrogels are formed by either physical crosslinking or chemical crosslinking. Physical crosslinking is typically a more rapid process but does not lead to the formation of mechanically resilient or stable hydrogels. On the other hand, chemical crosslinking leads to formation of more mechanically resilient hydrogels that are non-absorbable or absorbable with a predictable breakdown. Rapid chemical crosslinking, however, may require conditions that are incompatible with sensitive tissues.

For example, in photoinitiated free radical polymerization, very high intensities of light may be required, but such high light intensities may produce adverse photothermal effects. As another example, a high rate of free radical generation may be toxic to cells and tissue. Conversely, if an electrophilic and nucleophilic exchange type reaction is used to facilitate crosslinking, the reactions are typically slow and can take several to tens of minutes to proceed under physiological pH conditions. Thus slower crosslinking reactions, while less-toxic, pose a risk that the hydrogel may be displaced, diluted, or otherwise compromised at the deposition site during the time needed to accomplish chemical crosslinking.

Compositions prepared in accordance with the present invention employ a dual crosslinking approach to formation of hydrogels in situ. As used herein, the term "in situ" refers to formation of the hydrogel at the place of administration. Thus, for example, the reaction mixture compositions may be injected, sprayed, or otherwise applied to a site in need of augmentation, protection, or other therapy, and allowed to crosslink at the site of injection or delivery. Suitable sites may include any of a variety of tissues and organs within a living entity or cells, cell clusters, tissues, or disaggregated organs suitable for transplantation of culture or manipulation ex vivo.

Preferably, physical crosslinking of the hydrogel precursor solutions proceeds rapidly upon introduction,of the precurs r solutions at the deposition site, and serves to localize or confine the hydrogel forming precursors at that site. The resulting increased residence time facilitates the chemical crosslinking process, which may accordingly proceed at milder physiologically compatible conditions to form the final mechanically resilient hydrogel implant. Suitable components of a hydrogel forming composition comprising both physically crosslinkable polymers and chemically crosslinkable polymers are described hereinafter. Preferably, all of these compositions are chosen so as to be substantially water soluble.

Polymers Suitable for Physical Crosslinking

Physical crosslinking may be intramolecular or intermolecular or in some cases, both. For example, hydrogels can be formed by the ionic interaction of divalent cationic metal ions (such as Ca+2 and Mg+2) with ionic polysaccharides such as alginates, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, and amylopectin. These crosslinks may be easily reversed by exposure to species that chelate the crosslinking metal ions, for example, ethylene diamine tetraacetic acid. Multifunctional cationic polymers, such as poly(1-lysine), poly (allylamine), poly(ethyleneimine), poly(guanidine), poly (vinyl amine), which contain a plurality of amine functionalities along the backbone, may be used to further induce ionic crosslinks.

Hydrophobic interactions are often able to induce physical entanglement, especially in polymers, that induces increases in viscosity, precipitation, or gelation of polymeric solutions. For example, poly(oxyethylene)-poly (oxypropylene) block copolymers, available under the trade name of PLURONIC®, BASF Corporation, Mount Olive, N.J., are well known to exhibit a thermoreversible behavior in solution. Thus, an aqueous solution of 30% PLURONIC® F-127 is a relatively low viscosity liquid at 4° C. and forms a pasty gel at physiological temperatures due to hydrophobic interactions. Other block and graft copolymers of water soluble and insoluble polymers exhibit similar effects, for example, copolymers of poly(oxyethylene) with poly (styrene), poly(caprolactone), poly(butadiene) etc.

Techniques to tailor the transition temperature, i.e. the temperature at which an aqueous solution transitions to a gel due to physical linking, are per se known. For example, the transition temperature may be lowered by increasing the degree of polymerization of the hydrophobic grafted chain or block relative to the hydrophilic block. Increase in the overall polymeric molecular weight, while keeping the hydrophilic: lipophilic ratio unchanged also leads to a lower gel transition temperature, because the polymeric chains entangle more effectively. Gels likewise may be obtained at lower relative concentrations compared to polymers with lower molecular weights.

Solutions of other synthetic polymers such as poly(N-alkylacrylamides) also form hydrogels that exhibit thermoreversible behavior and exhibit weak physical crosslinks on warming. During spraying of thermoreversible solutions, cooling of the solutions may be expected from evaporation during atomization. Upon contact with tissue target at physiological temperatures, viscosity is expected to increase from the formation of physical crosslinks.

Similarly, pH responsive polymers that have a low viscosity at acidic or basic pH may be employed, and exhibit an increase in viscosity upon reaching neutral pH, for example, due to decreased solubility. Thus, the stability and reactivity of crosslinkable aqueous polymers can be controlled by appropriate selection of pH. For example, degradable esters are stable at pH 3–5, while reactivity for electrophilic-nucleophilic reactions is highest at elevated pHs.

For example, polyanionic polymers such as poly(acrylic acid) or poly(methacrylic acid) possess a low viscosity at acidic pHs that increases as the polymers become more solvated at higher pHs. The solubility and gelation of such polymers further may be controlled by interaction with other water soluble polymers that complex with the polyanionic polymers. For example, it is well known that poly(ethylene oxides) of molecular weight over 2,000 dissolve to form clear solutions in water. When these solutions are mixed with similar clear solutions of poly(methacrylic acid) or poly(acrylic acid), however, thickening, gelation, or precipitation occurs depending on the particular pH and conditions used (for example see Smith et al., "Association reactions for poly(alkylene oxides) and poly(carboxylic acids)," *Ind. Eng. Chem.*, 51:1361 (1959). Thus, a two component aqueous solution system may be selected so that the first component (among other components) consists of poly(acrylic acid) or poly(methacrylic acid) at an elevated pH of around 8–9 and the other component consists of (among other components) a solution of poly(ethylene glycol) at an acidic pH, such that the two solutions on being combined in situ result in an immediate increase in viscosity due to physical crosslinking.

Physical gelation also may be obtained in several naturally existing polymers too. For example gelatin, which is a hydrolyzed form of collagen, one of the most common physiologically occurring polymers, gels by forming physical crosslinks when cooled from an elevated temperature. Other natural polymers, such as glycosaminoglycans, e.g., hyaluronic acid, contain both anionic and cationic functional groups along each polymeric chain. This allows the formation of both intramolecular as well as intermolecular ionic crosslinks, and is responsible for the thixotropic (or shear thinning) nature of hyaluronic acid. The crosslinks are temporarily disrupted during shear, leading to low apparent viscosities and flow, and reform on the removal of shear, thereby causing the gel to reform.

Macromers Suitable for Chemical Crosslinking

Water soluble polymerizable polymeric monomers having a functionality >1 (i.e., that form crosslinked networks on polymerization) and that form hydrogels are referred to hereinafter as "macromers". Several functional groups may be used to facilitate chemical crosslinking reactions. When these functional groups are self condensible, such as ethylenically unsaturated functional groups, the crosslinker alone is sufficient to result in the formation of a hydrogel, when polymerization is initiated with appropriate agents.

In situ polymerized hydrogels also may be formed by crosslinking reactions caused by reaction of dissimilar functional groups that have a tendency to react under physiological conditions in timeframes relevant for in situ polymerization. Preferably, chemical crosslinking should result in an insoluble crosslinked gel having some physical integrity (e.g., a modulus greater than 0.5 KPa) within a period time useful in practicing the present invention, e.g., in a range of several minutes to a few hours.

Macromers useful for preparing the hydrogel formulations of the present invention therefore may contain functional or crosslinking or leaving groups that demonstrate activity towards other functional groups such as amines, imines, thiols, carboxyls, isocyanates, urethanes, amides, thiocyanates, hydroxyls, etc., that may either be naturally present in, on, or around tissue or may be optionally provided in the region as part of the instilled formulation required to effect the formation of the hydrogel.

Macromers for use in forming in situ formed hydrogels of the present invention generally comprise one or both of the following substantially water soluble components: (1) a water soluble crosslinking agent (WSCA); and (2) a water soluble crosslinkable polymer (WSCP).

The WSCA may be selected from any of a variety of in situ polymerizable macromers capable of forming hydrogel compositions. The WSCA may be capable of reacting with itself to form a self crosslinkable system, for example, a poly(ethylene glycol) multiacrylate macromer may be activated by various free radical initiating agents to crosslink with itself and form a hydrogel. The WSCA also may co-polymerize with similar functional groups to form the crosslinked network. For example, the poly(ethylene glycol) multiacrylate macromer may be co-polymerized with a mono or multifunctional acrylate, methacrylate or other ethylenically unsaturated moiety to form the hydrogel.

The WSCA also may be selected to form a hydrogel when it interacts with the WSCP under appropriate conditions. For example, the WSCA may be selected so that it has multiple (>1) electrophilic groups which can react with a suitable WSCP having multiple nucleophilic groups, as described hereinbelow. The resulting hydrogels may or may not absorb in vivo depending on the selection of the WSCP and the WSCA.

Thus, macromers may be selected from compositions that are biodegradable, polymerizable, and substantially water soluble macromers comprising at least one water soluble region, at least one degradable region, and statistically more than 1 polymerizable region on average per macromer chain, wherein the polymerizable regions are separated from each other by at least one degradable region and that the polymerizable groups are not ethylenically unsaturated or free radical polymerizable. The individual regions that comprise such macromers are described in detail below.

A variety of suitable crosslinking agents (WSCA) may be used in the present invention. Preferred crosslinking agents include a substantially water soluble polymeric backbone (A) that may be linear or branched, active crosslinking or leaving group portions (CG and CG'), that may or may not be identical, and optional chain extending segment (—CE—) that binds the water soluble polymer (A) portion and the crosslinking or leaving group portion (—CG or CG'). WSCA compounds generally may be represented by the following formula:

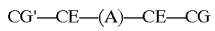

in which A is a di or multifunctional and substantially water soluble polymer selected from the group described hereinbelow in the section entitled "Water soluble region". —CG and CG' are either crosslinking or leaving groups such as a succinimidyl, maleimidyl, phthalimidyl, nitrophenyl, imidazolyl or tresyl groups or a functional group that reacts further with other electrophilic or nucleophilic functional groups.

If the functionality of A is increased beyond 2, additional crosslinking sites become available and more densely crosslinked networks result. The more densely crosslinked networks may have useful properties, such as more rapid solidification from the liquid precursors, higher strength, low swelling and shape change, increased strength and modulus, etc. If the WSCA is a self condensible crosslinker that reacts with itself or macromers that contain like functional groups, then —CG may be selected from functional groups that polymerize among themselves, when polymerization is initiated in the presence of appropriate initiating conditions, without the need for the WSCP.

Preferable functional groups in these situations include, without limitation, alkyl acrylates and cinnamates, norbornenes among others. Particularly preferred functional groups are acrylates, which are known in the art to exhibit rapid polymerization. Other appropriate crosslinking or leaving groups are described in greater detail hereinafter in the section entitled "Polymerizable Regions".

The WSCP may be selected from any of a variety of water soluble polymers that contain active functional groups that are reactive to electrophilic or nucleophilic crosslinking or leaving groups. These functional groups either may be present along the backbone of the polymer as a regularly or randomly spaced moiety or may be present at the end groups or as branched or grafted segments. The WSCP may be selected from any of a variety of substantially water soluble polymers as described hereinbelow in the section entitled "Water Soluble Regions/Polymers," provided that they contain statistically >1 functional group active towards crosslinking or leaving groups that are present in the added WSCA to enable the formation of a crosslinked or high molecular weight network.

(A) Water Soluble Regions/Polymers

Water soluble region/polymers preferred for use in the compositions of the present invention may be selected from any of a variety of natural, synthetic, or hybrid polymers the group consisting of poly(ethylene glycol), poly(ethylene oxide), poly(vinyl alcohol), Poly(allyl alcohol), poly (vinylpyrrolidone), other poly(alkylene oxides), such as poly(propylene glycol) ("PPG"); and poly(oxyethylated polyols), such as poly(oxyethylated glycerol), poly (oxyethylated sorbitol), and poly(oxyethylated glucose), poly(ethyleneimine), poly(allylamine), poly(vinyl amine), poly(aminoacids), poly(ethyloxazoline), poly(ethylene oxide)-co-poly(propyleneoxide) block copolymers, polysaccharides, carbohydrates, oligo or polypeptides, polynucleotides, proteins, and combinations thereof.

The foregoing polymers may be homopolymers or random or block copolymers and terpolymers based on the monomers of the above polymers, straight chain or branched, or substituted or unsubstituted similar to PEG, but having more than one active site available for reaction. In the case of selection of a WSCP, the reactive site should be capable of reacting with a crosslinking or leaving group from the crosslinking agent (WSCA).

In the event of selection of these water soluble regions for use as a component of the WSCA, more than one site should be available to be coupled to a crosslinking or leaving group, which may or may not be separated from the water soluble region by a chain extending segment or a spacer segment. The spacer or chain extending segment increases degree of association, thereby increasing reactivity and overall solubility. This in turn may provide bioabsorbability, enhanced viscosity, or otherwise advantageously affect the physical or chemical properties of either the WSCA or the final hydrogel composition.

Random copolymers of monomers that form water soluble polymers also may be used, for example, copolymers of vinyl amine and allyl alcohol. These type of random copolymers are preferred when the crosslinking reaction is mediated by nucleophilic or electrophilic functional groups. The water soluble region also may be selected from species that are capable of being rendered hydrophilic in a post-polymer reaction. For example, vinyl esters of carboxylic acids such as vinyl formate, vinyl acetate, vinyl monochloroacetate, and vinyl butyrate, may be copolymerized with the aforementioned copolymerizable macromolecular monomers. Subsequent to the copolymerization reaction, the polymeric backbone containing repeating monomeric units of these vinyl esters of carboxylic acids may be rendered hydrophilic by hydrolysis, so that the polymeric backbone comprises a polyvinyl alcohol.

Polymerizable species suitable for use in preparing a hydrophilic polymeric backbone of the macromers of the present invention include:

acrylic and methacrylic acid, water-soluble monoesters of acrylic and methacrylic acid in which the ester moiety contains at least one hydrophilic group such as hydroxy group, i.e., the hydroxy lower alkyl acrylates and methacrylates, typical examples of which include:
2-hydroxyethyl acrylate,
2-hydroxyethyl methacrylate,
2-hydroxypropyl acrylate,
2-hydroxypropyl methacrylate,
3-hydroxypropyl acrylate,
3-hydroxypropyl methacrylate,
diethylene glycol monomethacrylate,
diethylene glycol monoacrylate,
dipropylene glycol monomethacrylate, and
dipropylene glycol monoacrylate.

water-soluble vinyl monomers having at least one nitrogen atom in the molecule, examples of which include:
acrylamide,
methacrylamide,
methylolacrylamide,
methylolmethacrylamide,
diacetone acrylamide
N-methylacrylamide,
N-ethylacrylamide,
N-hydroxyethyl acrylamide,
N,N-disubstituted acrylamides, such as
N,N-dimethylacrylamide,
N,N-diethylacrylamide,
N-ethylmethylacrylamide,
N,N-dimethylolacrylamide, and
N,N-dihydroxyethyl acrylamide heterocyclic nitrogen containing compounds such as
N-pyrrolidone,
N-vinyl piperidone,
N-acryloylpyrrolidone,
N-acryloylpiperidine, and N-acryloylmorpholene,
N-vinyl pyrrolidinone,
N-Vinyl caprolactam,
N-vinyl acetate etc.

cationic functional monomers, such as vinyl pyridene quaternary ammonium salts and dimethyl aminoethyl methacrylate quaternary ammonium salts.

Suitable hydrophobic copolymerizable monomers also may be interpolymerized with the afore-described hydrophobic copolymerizable macromolecular monomers and the afore-described hydrophilic copolymerizable comonomers as long as the ultimate macromer or products of biodegradation are water soluble. Hydrophobic species may include the alkyl acrylate and methacrylates, e.g., methylacrylate or methacrylate, ethylacrylate or methacrylate, propylacrylate or methacrylate, butylacrylate or methacrylate, butylacrylate being preferred. Other suitable hydrophobic copolymerizable comonomers include vinyl chloride, vinylidene chloride, acrylonitrile, methacrylonitrile, vinylidene cyanide, vinyl acetate, vinyl propionate, and vinyl aromatic compounds such as styrene and alpha-methylstyrene, and maleic anhydride.

Suitable hydrophilic polyether polyols include adducts of ethylene oxide (hereinafter referred to as EO) or combinations thereof with one or more other alkylene oxides (hereinafter referred to as AO) to one or more compounds containing at least two active hydrogen atoms, for example, polyhydric alcohols (such as ethylene glycol and propylene glycol), polyhydric phenols, polyester polyols, amines, polycarboxylic acids and phosphorous acids. Addition of EO or combination of EO with AO, by random-addition, block-addition or combination of them (such as random-addition followed by block-addition), to active hydrogen atom-containing compounds may be carried out by methods which are per se known, with or without catalysts (such as alkaline catalysts, amine catalysts and acidic catalysts), under normal or an elevated pressure, in a single step or multi-stages.

Hydrophilic polyether polyols have equivalent weight (molecular weight per hydroxyl group) of usually 100–50,000, preferably 400–20,000, and oxyethylene content of usually at least 30%, preferably 50–90% by weight. Other polyols may include low molecular weight polyols and/or hydrophobic polyols that may be used as aqueous solutions or in conjunction with a water miscible organic solvent, or even as a neat liquid that is either liquid at body temperature or elevated temperatures that are tolerable without excessive tissue damage for short periods of time.

Examples of such polyols are polyhydric alcohols mentioned above; AO adducts (such as propylene oxide adducts) of active hydrogen atom-containing compounds as mentioned above (polyhydric alcohols and others); and polyester polyols (for example, condensation products of dihydric and/or trihydric alcohols (such as ethylene glycol, propylene glycol, 1,3- and 1,4-butane diols, 1,6-hexane diol, neopentyl glycol, diethylene glycol, glycerol, trimethylolpropane and the like) and/or polyether polyols (such as those described above) with dicarboxylic acids (aliphatic or aromatic dicarboxylic acids, such as glutaric, adipic, sebacic, fumaric, maleic, phthalic and terephthalic acids) or ester-forming derivatives thereof (anhydrides and lower alkyl esters, such as maleic and phthalic anhydrides, dimethyl terephthalate, and the like); ring-opening polymerization products of lactones (such as epsilon-caprolactone). Derivatives of poly (ethylene glycol) which are terminated with various functional groups such as diamino, tetraamino, or other nucleophilic groups also may be used.

Suitable water miscible solvents for use with relatively hydrophobic polymers are those that are biocompatible, pharmaceutically-acceptable, miscible with the polymer ingredient and water, and capable of diffusing into an aqueous medium, for example, tissue fluids surrounding the implant site, such as blood serum, lymph, cerebral spinal fluid (CSF) and saliva. Solvents useful in the liquid polymer solution include, for example, N-methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsufoxide, oleic acid, propylene carbonate, aromatic amides such as N,N-diethyl-m-toluamide, 1-dodecylazacycloheptan-2-one, and the like. Preferred solvents according to the invention include N-methyl-2-pyrrolidone, 2-pyrrolidone, dimethyl sulfoxide, ethyllactate, and propylene carbonate.

Preferred water soluble polymers (WSCP) may be selected from natural or synthetic proteins or polypeptide polycations such as polyamino acids, e.g., polyhistidine, poly(guanidine), polylysine, polyornithine, polyarginine, polyalanine-polylysine, poly(histidine, glutamic acid), polyalanine-polylysine, poly(phenylalanine, glutamic acid)-polyalanine-polylysine, poly(tyrosine, glutamic acid)-polyalamine-polylysine, collagen and gelatin; random copolymers of: arginine with tryptophan, tyrosine, or serine; glutamic acid with lysine; glutamic acid with lysine, ornithine, or mixtures thereof; polymers containing primary amine groups, secondary amine groups, tertiary amine groups or pyridinyl nitrogen(s), such as polyethyleneimine and modified polyethyleneimine with ethoxylation or epichlorihydrin (such as those available from BASF Corporation, Mount Olive, N.J.), polyallylamine, poly(vinyl amine), poly(aminoethyl acrylate), poly(diethyl amino ethyl acrylate), polyetheramine and polyvinylpyridine; and lipids such as phosphatidylethanolamine, phosphatidylserine, phosphatidylinositol, phosphatidyCGlycerol, dilaurylphosphatidic acid, dipalmitoyl phosphatidyl glycerol, and starburst dendrimers (having multiple amine functional groups such as those manufactured by Dendritech, Inc., Midland, Mich., and described in U.S. Pat. Nos. 4,568,737 and 4,507,466, to Tomalia et al.

(B) Degradable Regions

When used in the hydrogel-forming compositions of the present invention, the chain extending or spacer segment —CE—, may comprise any of several different types of divalent compounds. For example, compounds are commercially available having PEG as the water soluble portion A, and the —CG portion linked with a saturated dicarboxylic acid such as succinic acid to give a saturated diester linking moiety. Alternatively, an unsaturated dicarboxylic acid such as fumaric, maleic, phthalic or terephthalic acid may be used to give an unsaturated diester linking moiety.

—CE— could also be a diradical fragment such as a carbonate diradical represented by the formula, —C(O)—, a monoester diradical represented by the formula, —(CH$_2$)$_b$C(O)— where b is an integer from 1–5, a diester diradical represented by the formula, —C(O)(CH$_2$)C—C(O)— where c is an integer from 2–10 and where the aliphatic portion of the radical may be saturated or unsaturated, a dicarbonate represented by the formula —C(O)—O—(CH$_2$)$_d$—O—C(O)— where d is an integer from 2–10, or an oligomeric diradical represented by the formulas —R—C(O)—, —R—C(O)—(CH$_2$)$_c$—C(O)—, or —R—C(O)O—(CH$_2$)$_d$—O—C(O)— where c is an integer from 2–10, d is an integer from 2–10, and R is a degradable polymer or copolymer having 1–10 monomeric lactide, glycolide, trimethylene carbonate, caprolactone or p-dioxanone, poly (anhydride), poly(orthoester), poly(esteramide), polypeptide, polysaccharide, polynucleotide, glycosaminoglycan fragments etc.

The presence of the degradable regions is optional, depending on whether or not a degradable hydrogel is desirable for a certain application. It will be recognized that in certain applications, degradability is undesirable (e.g., for occluding arteriovenous malformations by embolization of the abnormal vasculature using in situ formed hydrogels). In this case the chain extending group may be selected from agents that provide a stable linkage, may be included because it beneficially provides some other physical or chemical property apart from degradability, or may be omitted altogether. In the event that degradability is a desirable attribute of the in situ formed hydrogels, the degradable region may be selected from any of a variety of polymers that undergo either hydrolytic, enzymatic, or thermal decomposition by bond scission of linkages to produce ultimately soluble and physiologically cleared molecules.

Preferable biodegradable polymers may be selected from the group consisting of poly ($\alpha$-hydroxy acids), poly (lactones), poly(amino acids), peptide sequences, oligonucleotides, poly(saccharides), poly(anhydrides), poly (orthoesters), poly(phosphazenes), and poly(phosphoesters), other ester, imine, phosphoester, disulfide, linkages etc. and combinations, copolymers, and blends thereof. In some cases the water soluble and the degradable region may be one and the same, for example, as in the case of proteins and poly(saccharides) that are degraded by naturally existing enzymes within the body.

(C) Polymerizable Regions

The crosslinking or leaving group, —CG, portion of the crosslinking agent is an activated crosslinking or leaving group that allows the crosslinking agent to react or chemically bind to free functional groups of another water soluble polymer. The other water soluble polymer may be either synthetic or naturally present in the physiological environment, such as a protein, polysaccharide, oligonucleotide, or glycosaminoglycan. Suitable crosslinking or leaving groups include acrylates, methacrylates, cinnamates, vinyl, allyl, succinimidyl, other imides such as maleimidyl and phthalimidyl, heterocyclic crosslinking or leaving groups such as imidazolyl, aromatic crosslinking or leaving groups such as a nitrophenyl, or fluorinated alkyl-sulfone crosslinking or leaving groups such as tresyl ($CF_3$—$CH_2$—$SO_2$—$O$—). It should be understood that addition water soluble or water dispersible smaller molecular weight species that may have functional groups suitable for co-polymerization with the WSCA also may be added to the hydrogel forming compositions.

The polymerizable end groups in the foregoing macromers consist of groups that react either within themselves, with added excepients, or with the surface of tissue to form a tissue protective coating. Polymerizable groups may be selected from nucleophilic groups and their salts that react further, for example, with acylating agents. Useful nucleophilic groups may include primary, secondary, or tertiary, or quaternary amino, amide, urethane, urea, hydrazide, or thiol groups among others. These functional groups may be present along the main chain of the water soluble macromer or present only at the end groups. When they are present along the main chain of the macromer, they may be evenly spaced, as in a blocky polymer or they may be randomly spaced.

For example, Shearwater Polymers, Inc., Huntsville, Ala., sells p-PEGs which contain pendant functional groups. Optionally these groups may be spaced from the polymeric main chain (either at the chain ends or along the backbone) by spacer groups that may contain ester linkages. The preparation of macromers containing amino acid esters of PEG is described, for example, in Zalipsky et al., "Esterification of Polyethylene Glycols," *J. Macromol. Sci. Chem.*, A21:839–845 (1984). The presence of such linkages can impart desirable properties such as speed of polymerization and predictable instability of the linkages. These nucleophilic functional group containing macromers optionally may be mixed with electrophilic group containing macromers to rapidly initiate polymerization.

Several nucleophilic and electrophilic functional groups are naturally present in the proteins, polysaccharides, glycosaminoglycans, and oligonucleotides that constitute tissue, cells, and organs. Thus, both nucleophilic and electrophilic macromers can react with appropriate naturally occurring functional groups in the absence of any additional externally added macromers. It has been determined, however, that reaction rates are more predictable, and the properties of the hydrogel are more predictable, if both components are added externally so as to initiate polymerization and formation of the hydrogel.

Electrophilic groups useful for reacting with aforementioned nucleophilic groups include carboxyl groups that may or may not be separated from the polymeric main chain (either at the chain ends or along the backbone) by spacer groups that may contain ester linkages (for example esters of succinic acid, carboxymethyl esters, esters of propionic, adipic, or amino acids). Other useful groups include isocyanate, thiocyanate, N-hydroxy succinamide esters, such as succinamide and succinamide groups that are spaced by groups such as esters or amino acids, including succinimidyl succinates, succinimidyl propionates, succinimidyl succinates succinimidyl esters of carboxymethylated water soluble polymers, benzotriazole carbonates, and any of a variety of carbodiimides may also be selected.

PEG succinimidyl succinates, PEG succinimidyl propionates, succinimidyl esters of amino acid or carboxymethylated PEG, and PEG succinamidyl succinamides are particularly suitable as electrophilically active macromers for reacting with nucleophilic group containing macromers due to their high reactivity at physiological pH and speed of polymerization. Other useful electrophilic macromers may contain functional groups such as glycidyl ethers (or epoxides) or hydroxyl group containing polymers that have been activated with 1,1 Carbonyl diimidazole (for example PEG-oxycarbonylimidazole) or p-nitropheynyl chlorocarbonates (e.g., PEG nitrophenyl carbonate), tresylates, aldehydes, isocyanates, etc. Other groups reactive towards nucleophilic moieties may include for example anhydrides.

Thus, for example, a polymer of maleic anhydride when copolymerized with allyl or vinyl group containing water soluble polymers (such that the vinyl or allyl or other ethylenically unsaturated functionality is 1 per molecule or lower) forms a water soluble co-polymer that contains anhydride groups along the backbone. These anhydride groups can be reactive towards any of the various nucleophilic groups mentioned before. Other electrophilic groups that are more selective towards specific nucleophiles (such as sulfahydryl groups) also may be used such as vinylsulfone, maleimide, orthopyridyl disulfide or iodoacetamide containing macromers.

The crosslinking agents may be prepared using known processes, procedures or synthetic methods such as the procedures described in U.S. Pat. No. 4,101,380 to Rubenstein et al. or U.S. Pat. No. 4,839,345 to Doi et al., the procedure described in International Application Ser. No. PCT/US90/02133 filed Apr. 19, 1990 or the procedure reported by Abuchowski et al., "Cancer Therapy with Chemically Modified Enzymes. I. Antitumor Properties of Polyethylene Clycol-Asparaginase Conjugates," *Cancer Biochem. Biophys.*, 7:175–186 (1984).

In addition, more than one type of electrophilic group or nucleophilic group may be present as a part of a macromer chain, so that multiple levels of reactivities may be built into the materials. In fact, both electrophilic and nucleophilic groups may be built into the same molecule. In this case, the WSCP and the WSCA are not separate and premature crosslinking may be prevented by preparing the solution at a pH where the reactivity between these functional groups is low, subsequent alteration of pH by mixing with a buffered solution then may be used to initiate the crosslinking reaction.

The concentration and number of the functional groups also may be varied to obtain different rates of reactivity. For example, the pH of the solutions may be varied to control rates of reaction and the properties of the crosslinked hydrogel that results also may be tailored by appropriate selection of the reactive macromers. For example, a higher molecular weight between crosslinks may lead to the formation of a more flexible hydrogel having a lower modulus.

The hydrogel compositions of the present invention also may be advantageously polymerized outside the physiological environment and formed into capsules, tablets, films, microspheres, or the like. The hydrogel compositions may include conventional pharmaceutical carriers or excipients, adjuvants, etc. Hydrogel matrices in the form of discs, slabs or cylinders may be used as implants, while microspheres may be applied as subcutaneous, intramuscular, intravenous or intra-arterial injectables. The hydrogel matrices also may be formed around other devices for medical or other use so as to form coatings, composite devices, or preformed plugs, rods, or other shaped objects.

Applications of In Situ Formed Materials

In situ formed hydrogel materials prepared in accordance with the present invention may be advantageously used in numerous medical and surgical applications. While not attempting to be exhaustive, several illustrative applications for hydrogel compositions of the present invention are described:

U.S. Pat. No. 5,266,326 to Barry et al. describes a method for situ modification of alginate and formation as a spinal implant for use in postsurgical adhesion prevention.

U.S. Pat. No. 3,949,073 to Daniels et al. describes a process for augmenting connective mammalian tissue with an in situ polymerizable native collagen solution.

U.S. Pat. No. 4,195,129 Fukui et al. describes photocurable resins and method for immobilizing enzymes and microbial cells using such resins.

U.S. Pat. No. 5,529,914 to Hubbell et al. describes photocurable resins, mainly based on acrylated water soluble polymers, that form biocompatible membranes around biological materials. The membranes may be used as a covering to encapsulate biological materials or biomedical devices, as a "glue" to cause more than one biological substance to adhere together, or as carriers for biologically active species.

U.S. Pat. No. 5,626,863, also to Hubbell et al., describes synthetic polymerizable water soluble molecules useful for various gluing, sealing, coating, and plugging applications in surgery.

Delivery of Bioactive Species

The in situ formed hydrogels of the present invention further may be applied in conjunction with bioactive molecules that either are dissolved or dispersed within the hydrogels. The dispersed or dissolved drugs may either be present as a particulate suspension that may or may not be further contained in a secondary containment membrane or coating, microspheres or microcapsule. The materials for such secondary coating and containment also may be selected from any of a variety of biodegradable natural or synthetic hydrophobic materials that provide a resistance to diffusion of small molecules, especially water soluble small molecules.

The biologically active molecules may be selected from the group consisting of proteins (including growth factors and enzymes that may demonstrate bioactivity), carbohydrates, nucleic acids (both sense and antisense as well as gene fragments for gene therapy), organic molecules, inorganic biologically active molecules, cells, tissues, and tissue aggregates. The beneficial drugs are known in the art in *Pharmaceutical Sciences*, by Remington, 14th Ed., 1979, published by Mack Publishing Co.; *The Drug, The Nurse, The Patient, Including Current Drug Handbook*, by Falconer et al., 1974–1976, published by Saunder Company; and *Medicinal Chemistry*, 3 rd Ed., Vol. 1 and 2, by Burger, published by Wiley-Interscience Co.

Drugs delivered by the in situ formed hydrogel of the present invention also may serve to supplement the overall therapeutic regimen for the particular patient by delivering a drug or a combination of drugs that address a disease state. For example, physiologically active materials or medicinal drugs, e.g., agents affecting central nervous system, anti-allergic agents, cardiovascular agents, agents affecting respiratory organs, agents affecting digestive organs, hormone preparations, agents affecting metabolism, antitumor agents, antibiotic preparations, chemotherapeutics, antimicrobials, local anesthetics, antihistaminics, antiphlogistics, astringents, vitamins, antifungal agents, peripheral nervous anesthetics, vasodilators, crude drug essences, tinctures, crude drug powders, hypotensive agents, and the like, may be delivered.

Drugs suitable for delivery through using in situ formed hydrogels include both water soluble, partially water soluble, and lipophilic drugs. The drugs may be small molecules or macromolecular in nature. Particular water-soluble polypeptides which may be used in this invention are, for example, oxytocin, vasopressin, tissue plasminogen activator, urokinase, streptokinase, streptodornase, ancrod, and other fibrinolytic enzymes, adrenocorticotrophic hormone (ACTH), epidermal growth factor (EGF), transforming growth factor antagonists, prolactin, luliberin or luteinizing hormone releasing hormone (LH-RH), LH-RH agonists or antagonists, growth hormone, growth hormone releasing factor, follicle stimulating hormone, insulin, somatostatin, bombesin antagonists, glucagon, interferon, gastrin, tetragastrin, pentagastrin, urogastrone, secretin, calcitonin, enkephalins, endomorphins, angiotensins, renin, bradykinin, bacitracins, polymyzins, colistins, tyrocidin, gramicidines, and synthetic analogues and modifications and pharmaceutically-active fragments thereof, monoclonal antibodies and soluble vaccines.

The water-soluble drugs that are deliverable using the hydrogel compositions of the present invention are not specifically limited. Examples of such drugs include peptides having biological activities, other antibiotics, antitumor agents, antipyretics, analgesics, anti-inflammatory agents, antitussive expectorants, sedatives, muscle relaxants, antiepileptic agents, antiulcer agents, antidepressants, anti-allergic agents, cardiotonics, antiarrhythmic agents, vasodilators, hypotensive diuretics, antidiabetic agents, anticoagulants, hemostatics, antituberculous agents, hormone preparations, narcotic antagonists, bone resorption inhibitors, angiogenesis inhibitors and the like.

Examples of antitumor agents include bleomycin hydrochloride, methotrexate, actinomycin D, mitomycin C, vinblastine sulfate, vincristine sulfate, daunorubicin hydrochloride, adriamycin, neocarzinoszatin, cytosine arabinoside, fluorouracil, tetrahydrofuryl-5-fluorouracil krestin, picibanil, lentinan, levamisole, bestatin, azimexon, glycyrrhizin, poly I:C, poly A:U, poly ICLC, cisplatin and the like The terms "cytokine" and "growth factor" are used to describe biologically active molecules and active peptides (which may be either naturally occurring or synthetic ) that aid in healing or regrowth of normal tissue, including growth factors and active peptides. The function of cytokines is two-fold: 1) to incite local cells to produce new collagen or tissue, or 2) to attract cells to a site in need of correction. For example, one may incorporate cytokines such as interferons (IFN), tumor necrosis factors (TNF), interleukins, colony stimulating factors (CSFs), or growth factors such as osteogenic factor extract (OFE), transforming growth factor (TGF) alpha, TGF-$\beta$_(including any combination of TGF-$\beta$s), TGF-$\beta$1, TGF-$\beta$2, platelet derived growth factor (PDGF-AA, PDGF-AB, PDGF-BB), acidic fibroblast growth factor (FGF), basic FGF, connective tissue activating peptides (CTAP), $\beta$-thromboglobulin, insulin-like growth factors, erythropoietin (EPO), nerve growth factor (NGF), bone morphogenic protein (BMP), osteogenic factors, and the like.

Suitable biologically-active agents for use in the invention also include oxygen radical scavenging agents such as superoxide dismutase or anti-inflammatory agents such as hydrocortisone, prednisone and the like; antibacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, ribavirin, interferons and the like; analgesic agents such as salicylic acid, acetaminophen, ibuprofen, flurbiprofen, morphine and the like; local anesthetics such as lidocaine, bupivacaine, benzocaine, mepivacaine, pyrrocaine, bupivacaine, prilocaine, etidocaine and the like; vaccines such as hepatitis, influenza, measles, rubella, tetanus, polio, rabies and the like; central nervous system agents such as a tranquilizer, B-adrenergic blocking agent, dopamine and the like; growth factors such as and the like; hormones such as progesterone, antihistamines such as diphenhydramine, chlorphencramine and the like; cardiovascular agents such as digitalis, nitroglycerine, papaverine, streptokinase and the like; vasodilators such as theophylline, niacin, minoxidil, and the like; and other like substances.

The biologically-active agent may stimulate a biological or physiological activity with the animal. For example, the agent may act to enhance cell growth and tissue regeneration, function in birth control, cause nerve stimulation or bone growth, and the like. Examples of useful biologically-active agents include a substance, or metabolic precursor thereof, which is capable of promoting growth and survival of cells and tissues, or augmenting the functioning of cells, as for example, a nerve growth promoting substance such as a ganglioside, a nerve growth factor, and the like; a hard or soft tissue growth promoting agent such as fibronectin (FN) and the like; a bone growth promoting substance such as hydroxyapatite, tricalcium phosphate, and the like.

Since the permeability of hydrogels to small molecular weight drugs is known to be high, release rate modifying agents may be used in conjunction with hydrogels of the current invention. These agents may be used to control the release of therapeutic substances from within the hydrogel to the physiologic surrounding. Typically, this involves slowing the release by providing a secondary containment, diffusion resistance, ionic or other type of bonding that results in the release of the therapeutic substance being slowed. Useful release rate modification agents include, for example, organic substances which are water-soluble, water-miscible, or water-insoluble (i.e., water immiscible), with water-insoluble substances preferred.

The release rate modification agent is preferably an organic compound that substitutes as the complementary molecule for secondary valence bonding between polymer molecules, and increases the flexibility and ability of the polymer molecules to slide past each other. Such an organic compound preferably includes a hydrophobic and a hydrophilic region so as to effect secondary valence bonding. Preferably, the release rate modification agent is compatible with the combination of polymers and solvent used to formulate the polymer solution, and is a pharmaceutically-acceptable substance.

Useful release rate modification agents include, for example, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as $C_6$–$C_{12}$ alkanols, 2-ethoxyethanol, and the like.

The release rate modification agent may be used singly or in combination with other such agents. Suitable combinations of release rate modification agents include, for example, glycerin/propylene glycol, sorbitol/glycerine, ethylene oxide/propylene oxide, butylene glycol/adipic acid, and the like. Preferred release rate modification agents include dimethyl citrate, triethyl citrate, ethyl heptanoate, glycerin, and hexanediol.

Delivery Systems for In Situ Formed Hydrogels

Site specific or in situ transformation of the hydrogel materials of the present invention may be enabled using a number of previously known delivery devices. Generally, delivery systems suitable for delivering the hydrogel systems of the present invention will enable injection of a WSCA solution and a WSCP solution separately, or as a mixture. Alternatively, the components may be mixed together and applied as spray on tissues requiring a topical application.

One preferred embodiment for delivering the in situ formed hydrogels of the present invention includes a plurality of syringe bodies having equal effective strokes, where one of the syringe bodies has a cross sectional area larger or smaller than the other one. The WSCP solution and WSCA solution preferably are stored in separate barrels of a multi-barreled syringe until ready for use and the storage conditions and buffers are chosen so that the agents retain their activity over a convenient period of time.

In another application method, the two parts of the hydrogel forming system are added to a multi-chamber syringe, wherein the two barrels of the syringe are attached to a "Y" connection which is fitted to a spiral mixer nozzle. As the two components are pressed out of the syringe, they mix together in the nozzle and may be directly applied to the tissue as needed in a relatively uniform, controlled manner. Alternatively, the mixed components may be injected into tissue if the nozzle is further connected to a needle.

Injectable reaction mixture compositions also could be injected percutaneously by direct palpation, such as by placing a needle inside the vas deferens and occluding the same with the injected bulking substance, thus rendering the patient infertile. The compositions may be injected through a catheter or needle with fluoroscopic, sonographic, computed tomography, magnetic resonance imaging or other type of radiologic guidance. This would allow for placement or injection of the in situ formed hydrogel either by vascular access or percutaneous access to specific organs or other tissue regions in the body, wherever a bulking agent is required.

Suitable sites for augmentation of tissue may be intradermal or subcutaneous regions for augmenting dermal support, at the site of bone fractures for wound healing and bone repair, and within sphincter tissue for sphincter augmentation (e.g., for restoration of continence). Formulations of such hydrogels also may be used to coat other types of implants for long-term use in the body, such as catheters, cannulas, bone prostheses, cartilage, replacements, minipumps and other drug delivery devices, artificial organs and blood vessels, meshes for tissue reinforcement, etc. Hydrogel compositions also may be used to coat platinum wires, which then are administered to the site of an aneurysm via catheter. Such surface treatment renders the implants nonimmunogenic and reduces the incidence of foreign body reaction.

Further, a laparoscope or thoracoscope may be used to inject the in situ hydrogels of the present invention to any intraperitoneal or extraperitoneal or thoracic organ. For example, the hydrogel precursors could be injected in the region of the gastroesophageal junction to correct gastroesophageal reflux. Such a procedure could be performed either with a thoracoscope, by injecting the substance in the esophageal portion of the gastroesophageal region, or via a laparoscope, by injecting the substance in the gastric portion of the gastroesophageal region, or by a combined approach.

In addition to its use for the endoscopic treatment of reflux, the hydrogel system of the present invention may also be applicable for the treatment of other medical conditions, such as urinary and rectal incontinence, dysphonia, plastic reconstruction, and wherever an injectable permanent biocompatible material is needed. Methods for using an injectable polymer for delivering isolated cells via injection are described, for example, in WO 94/25080, which is incorporated herein by reference in its entirety.

Several types of catheters, injectors, endoscopic devices and devices used during open surgical procedures are known, and may be readily modified to deliver the components of the hydrogel systems of the present invention. No attempt is made to be comprehensive in the description of such previously known devices, and the following examples are intended to be merely illustrative:

U.S. Pat. No. 3,833,003 to Taricco describes an intravascular catheter having a balloon that may be inflated to occlude a blood vessel and another lumen to inject a medication.

U.S. Pat. No. 5,612,050 to Rowe et al. describes an apparatus and method for local application of polymeric material to the surface of tissue.

U.S. Pat. No. 5,665,063 to Roth et al. describes methods for applying intraluminal photopolymerized gels as layers to the interior surface of body lumens and spaces.

U.S. Pat. No. 5,213,580 to Slepian describes a catheter system for stabilizing and sealing the interior surface of a body vessel or organ using a biodegradable polymer.

U.S. Pat. No. 5,385,561 to Cerny describes apparatus and methods for injecting a viscous material into tissues.

U.S. Pat. No. 5,588,960 to Edwards et al. describes a transurethral needle delivery device with cystoscope for injecting collagen-based tissue bulking agents for treating urinary incontinence.

U.S. Pat. No. 5,366,498 to Brannan et al. describes a device for treating fine superficial facial lines comprising a syringe fitted with a 31–33 gauge needle and an aqueous suspension of collagen.

U.S. Pat. No. 5,304,147 to Johnson et al. describes an injection syringe useful for injecting high viscosity fluids or pastes, such as collagen or polytetrafluoroethylene paste, particularly in endoscopic applications.

The hydrogel compositions of the present invention may be advantageously locally administered to form hydrogel implants in situ using a variety of catheters, endoscopic sprayers and other applicators known in the art.

EXAMPLES

Example 1

Preparation of a WSCA

A water soluble polymer such as polyethylene glycol and a suitable acid anhydride are dissolved in a suitable polar organic solvent in the presence of base and refluxed for a period of time sufficient to form a polyethylene glycol diester diacid. The diester diacid then is reacted with a crosslinking or leaving group such as an N-hydroxy imide compound in a suitable polar organic solvent in the presence of dicyclohexyl-carbodiimide or other condensing agents and stirred at room temperature to form a bifunctional crosslinking agent.

Alternatively, polyethylene glycol and a suitable dicarboxylic acid chloride or bischloroformate is dissolved in a suitable polar organic solvent for a period of time sufficient to form the mixed acid chloride polyethylene glycol ester or mixed chloroformate polyethylene glycol ester. The mixed esters then are reacted with a compound such as an N-hydroxy imide compound in a suitable polar organic solvent and stirred at an elevated temperature for a period of time sufficient to form a bifunctional crosslinking agent.

Activated forms of PEG, including activated forms of mPEG, may be prepared using commercially available reactants. One form of activated PEG that may be particularly useful in connection with the present invention is mPEG-succinate—N-hydroxysuccinimide ester (SS-PEG). See, e.g., Abuchowski et al., "Cancer Therapy with Chemically Modified Enzymes. I. Antitumor Properties of Polyethylene Clycol-Asparaginase Conjugates," *Cancer Biochem. Biophys.*, 7:175–186 (1984). Activated forms of PEG such as SS-PEG react with proteins under relatively mild conditions.

Other activated forms of PEG-based water soluble crosslinking agents are commercially available from Shearwater Polymers, Huntsville, Ala. These forms include particularly preferred compositions such as PEG derivatives having esters of succinimidyl succinates, succinimidyl carbonates, succinimidyl glutarate, succinimidyl propionates, succinimidyl succinates succinimidyl esters of carboxymethylated PEG, benzotriazole carbonates, norleucine PEG, and any of a variety of carbodiimides. Different activating groups can be attached to one or both ends of the PEG molecule. For example, PEG can be derivatized to form difunctionally activated PEG propionaldehyde or PEG glycidyl ether.

Example 2

Synthesis of a WSCA with a Dearadable Chain Extender 100 g of PEG (mol. wt. 3,350), 600 ml of toluene, and 1 drop of 0.33 M stannous caprylate solution in xylene are added to a flask with a continuous nitrogen purge. The solution is heated to reflux and 100 ml of toluene removed by distillation. The solution then is cooled to room temperature and 34 g of glycolide (Boehringer Ingleheim KG, Ingleheim, Germany) is added to the flask and the reaction mixture refluxed under nitrogen for 16 hours.

The copolymer reaction mixture is precipitated by pouring it in a thin stream into an excess of hexane and collecting the precipitate by filtration. The copolymer then is placed in a flask with 1000 ml of dichloromethane and 14 g of succinyl chloride, and the solution is refluxed under nitrogen overnight (16 hours). 17 g of N-hydroxysuccinimide is be added to the flask and refluxing continued for another overnight period. A white solid is obtained by precipitation from hexane as described above. The precipitate is dried under vacuum and stored in a desiccator. The structure of the product may be confirmed by NMR analysis.

Example 3

Tissue Augmentation with in Situ Formed Hydrogels

The compositions of the WSCA described in example 2 above are dissolved at a concentration of 20% w/w in phosphate buffered saline, which additionally contains 18% w/w of dissolved PLURONIC®F-127, at a pH of 5 and at 4° C. temperature to form a "WSCA solution". A WSCP such as poly(l-lysine) is dissolved in a sodium borate buffered solution at a pH of 11 at a concentration of 5% w/w which additionally contains PLURONIC®F-127, at a concentration of 18% w/w, at 4° C. temperature to form a "WSCP solution".

The WSCA solution and WSCP solution are drawn into a multi-chamber syringe such as described hereinabove, and injected onto or into tissues in need of augmentation. The syringe body preferably includes multiple chambers, with the WSCA solution and the WSCP solution being stored in separate chambers in lyophilized form and a solvent being contained in a remaining chamber. The WSCA and WSCP solutions and solvent are formulated into a flowable form and injected into patients, such as into facial areas, to provide soft tissue augmentation. As the plunger of the syringe is depressed and the material is injected beneath the skin, the components mix in the needle of syringe and crosslink in situ. Some of the activated polymer molecules additionally may crosslink to the patient's own proteins and other natural materials to anchor the implant in place.

Preferably, contact of the solutions (which are at room temperature or cooler), with tissue at warmer physiological temperatures will result in an immediate increase in viscosity and gelation due to physical crosslinking. Within about 1–2 minutes a firm gel should result due to the subsequent chemical crosslinking.

To control meshwork formation, the hydrogel precursor solutions of the present invention also may include colored indicator substances such as phenol red (0.04–0.008%), thymol blue (0.04–0.1%), or furoxone (0.02–0.4%), rivanol (0.45-0.75%) or picric acid (0.01–0.03%). (All percentages are w/v.) As a result, a color change, such as a green color, will be observed after mixing or penetration of these colored substances (e.g., one is blue, other is yellow).

Example 4

Coating of Medical Devices

Coating of other surgical devices or implants with hydrogels of the current invention may be accomplished by dipping the implant into a solution containing WSCP solution and then exposing the coating to a WSCA solution to cause the onset of crosslinking. Optionally, the coating may be allowed to dry as crosslinking is completed. The dried coated device is stored stably until use and may be optionally rehydrated by being placed in an aqueous environment prior to use. One may pour, spray, brush, or otherwise apply the reaction mixture to the implant if dipping is not feasible. Alternatively, one may use flexible sheets or membranous forms of the conjugate to wrap the object, sealing corners and edges with reaction mixture.

It is contemplated in a "priming" method of delivering the hydrogel system of the present invention that one component first is used to establish a mechanical or chemical linkage with the underlying surface, e.g., by working the reaction mixture in its fluid form within the cracks and crevices, even microscopic in nature, of the device, either biologic, biohybrid, or manmade in nature. The other component is then administered to effect the crosslinking process. Other WSCA or WSCP species may be used for priming than those that are used to form the actual coating, for example, when the main reason for the priming layer is to achieve good adherence, while the coating layer is responsible for some enhanced property for the device being coated.

The surface of materials having a certain degree of surface texture, such as woven dacron, dacron velour, and expanded poly(tetrafluoro-ethylene) (ePTFE) membranes, and can be easily treated with hydrogel. Textured and macroporous surfaces allow greater adhesion of the hydrogel to the material surface, allowing the coating of relatively hydrophobic materials such as PTFE and poly(ethylene terephthalate) (PET) without the use of additional agents.

Example 5

Enhanced Properties of Coated Devices

Devices that have been coated with hydrogels of the current invention or with any hydrogels (absorbable or otherwise for that matter) may be expected to have superior properties compared to either the uncoated device or the hydrogel by themselves individually. Enhanced properties that may result include physical properties such as tear resistance for absorbable meshes. Thus, for example if a mesh of knitted or woven oxidized regenerated cellulose (such as Surgicel® or Interceed®, marketed by Ethicon, Inc., New Brunswick, N.J., is coated with a hydrogel composition as described in example 3, the pullout strength of a suture placed within this composite mesh is superior to that of the uncoated mesh or of the hydrogel film by itself.

Other superior physical or biological properties are expected including, for example, reduced interfacial tension in an aqueous surrounding, reduced potential for tissue ingrowth and reaction, better pH buffering capacity, better leakproofness, increased lubricity, improved hemocompatibility, reduced protein adsorption, reduced calcification, reduced immunogenicity, reduced allergenicity, improved flexibility or drapability, etc.

Example 6
Coating of ePTFE Vascular Grafts

Polytetrafluoroethylene is a polymeric material having extensive applications in the surgical and medical field. Several fabrics, sheets, and vascular grafts are made from expanded PTFE (ePTFE) materials. The surface of these materials is highly hydrophobic and thus application of aqueous based coatings to ePTFE based materials is difficult, because the coatings have a tendency not to adhere.

In addition, ePTFE based vascular grafts have a drawback that when sutures are placed in these materials, the needle hole is incompletely filled by the suture. This in turn often leads to leaks and in the case of vascular grafts, bleeding. U.S. Pat. No. 5,152,782 to Kowligi et al. describes use of a polyurethane-based coating applied to ePTFE vascular grafts to reduce anastomotic leakage. U.S. Pat. No. 5,509,899 to Fan et al. describes the formation of a hydrogel coating, comprising monomeric units polymerized from organic solvents, on balloon catheters to increase lubricity. U.S. Pat. No. 4,979,459 to Guire et al. describes the formation of hydrogel type coatings on implants. A method is described below for applying a hydrogel-based coating to ePTFE substrates that overcomes some of the drawbacks associated with the foregoing previously known methods.

A 12 mm diameter GORE-TEX® vascular graft (GORE-TEX® is a registered trademark of W. L. Gore, Inc., Newark, Del.) was incised to create a 5 mm long opening. This opening as sutured shut using a 7–0 suture spaced at 1 mm intervals. The vascular graft was pressurized with saline solution and a weeping of saline at the suture line was evident. A photopolymerizable solution of 20 K PEG terminated with acrylate end groups was prepared in saline at a concentration of 10% w/w containing 600 ppm of IRGACURE® 651 (IRGACURE® is a registered trademark of Ciba Specialty Chemicals Corp., Switzerland) and 15% PLURONIC® F-127, (PLURONIC® is a registered trademark of BASF Corporation, Mount Olive, N.J.), as a dispersant and physical crosslinker.

A couple of drops of acetone or isopropyl alcohol were applied to the suture line with a brush and this was immediately followed by application of the photopolymerizable solution. The vascular graft was maintained at an temperature of 37° C. Physical crosslinking of the photopolymerizable solution resulted in a perceptible increase in viscosity of the solution on application. Subsequent exposure of the solution to long wave ultraviolet light resulted in a hydrogel formation, which was adhered to the ePTFE material. The hydrogel resisted suture line weeping to pressures in excess of arterial pressures. If no acetone or isopropyl alcohol was used in the "priming" step, the resulting hydrogel was seen to be non-adherent and easily peeled off the suture line.

Example 7
Protection of Sensitive Tissue

Preformed or in situ formed hydrogels pieces of appropriate shape may be useful in protecting sensitive tissues, especially during the critical wound healing stage. Corneal shields are absorbable wound dressings for the eye used to protect and lubricate the eye and to promote healing following cataract surgery, corneal grafts, or abrasions or burns of the cornea. The shields are transparent, "hug" the eye like a contact lens, and disappear after approximately 12 hours to 3 days in the eye. Such products have heretofore been prepared from collagen and are just beginning to gain favor with ophthalmologists.

It is estimated that corneal shields could be used to treat the more than 2.5 million eye surgeries, injuries or burns that occur in the United States each year, including 1.5 million cataract surgeries, 40,000 corneal grafts, and one million eye injuries. Corneal shields are now used in 3–5% of the applicable surgeries. Hydrogels, such as those described in example 3 may be used for the formation of contact lens shaped hydrogels that may be stored in a dehydrated form and rehydrated prior to use. The synthetic nature of such hydrogels may provide significant advantages to the patient, since collagen based materials are often associated with allergic reactions and pose a risk of disease transmission.

Example 8
Prevention of Postsurgical Adhesions

Pericardial adhesions may severely complicate re-operation by increasing the risk of damaging vital structures, prolonging operation time and causing increased morbidity and mortality. Several methods have been suggested to limit postoperative pericardial adhesions, including implantation of biological or synthetic patches, with mixed results.

In accordance with one aspect of the present invention, a sheet of hydrogel, optionally reinforced by an embedded matrix type material such as a mesh of oxidized regenerated cellulose or Vicryl mesh, may be sutured into place over the heart and along the edges of the original pericardial sac. Over a period of time, such a hydrogel composite is expected to resorb and be replaced by autogeneous tissue without formation of postsurgical adhesions. This type of hydrogel composite material also may be advantageously used in other medical applications, for example, as a replacement for dura mater in cranial or spinal surgery, as a barrier to adhesion formation in various abdominal and pelvic procedures, etc.

Example 9
In Situ Formed Hydrogels as a Liquid Embolic Material

Various embolic materials have been used in endovascular treatment in the central nervous system, such as cyanoacrylates, ethylene-vinyl alcohol copolymer mixtures (EVAL), ethanol, estrogen, poly(vinyl acetate), cellulose acetate polymer, poly (vinyl alcohol) (PVA), gelatin sponges, microfibrillar collagen, surgical silk sutures, detachable balloons, and coils. The goal of embolization is to selectively obliterate an abnormal vascular structure while preserving the blood supply to surrounding normal tissues. This is typically accomplished using fluoroscopic equipment that visualizes the materials in the body—low-profile soft microcatheters which allow superselective catheterization into the brain— and embolic materials. To date, no safe rapidly polymerizing aqueous based liquid embolic material has been proposed. Such a material and a method to achieve embolization is described below.

A 37° C. thermostat-controlled reservoir, tube pump, Y-connector (Target Therapeutics, Fremont, Calif., USA) and a glass tube (inner diameter of 1.7 mm and outer diameter of 3.0 mm) are connected together in series via poly(vinyl chloride) tubes. The tube pump is used to generate a flow of 37° C. saline in the glass tube at a flow rate near that found in cerebral arteries. A microcatheter formed from an extrusion that having four lumens is used, in which one of the lumens is employed as a guidewire lumen. Another lumen is used to inflate a balloon that prevents retrograde flow of the embolic material, which is discharged from the other two lumens as a two part solution system of the WSCA solution and WSCP solution, respectively.

The catheter is inserted into the glass tube through the Y-connector. The WSCP and WSCA solutions are prepared as in example 3 above. A double barrel syringe as is described hereinabove is used to inject the liquid embolic material to occlude the glass tube, simulating occlusion of a cerebral artery.

Example 10
Microencapsulation of Tissue

Selective liver cell transplantation, in place of liver transplantation, may provide a method to engineer new liver tissue and treat multiple patients using a single donor liver or part thereof. The amazing regenerative ability of liver suggests that even a small number of hepatocytes could grow to a functionally significant tissue mass if the proper environment is provided. Identification and isolation of liver stem cells may ultimately allow a large number of autologous hepatocytes suitable for transplantation to be grown in vitro from a small liver biopsy.

Additionally, as techniques to transplant hepatocytes and promote engraftment of these cells are developed, such an approach could be utilized to transplant genetically manipulated cells into a patient to correct single gene defects. The native liver then could be left in place to perform the majority of the critical liver functions, while the engineered tissue could provide the single missing function. Such techniques would alleviate the need for costly whole organ transplantation, and may allow earlier intervention in the disease progression.

U.S. Pat. No. 5,624,840 to Naughton et al. describes a three dimensional culture technique for liver cells that extends survival of such cells in vitro and in vivo. That patent, however, does not teach how to protect these nascent tissues from the host immune system, and allograft or xenograft rejection may be expected to occur upon transplantation of such tissues. This example describes a technique to encapsulate individual cells or cell clusters into hydrogels that are formed in situ to make microspheres suitable for transplantation.

Disaggregated liver cells harvested from a liver biopsy are be dispersed in a WSCP solution (such as poly(1-lysine) at a concentration of 5% w/w and then sprayed using an annular co-extrusion arrangement wherein the internal channel contains the cell suspension and the outer channel carries sterile air that shears off the droplets. The droplets are allowed to fall into a bath containing a filter sterilized solution of a WSCA prepared as described in example 1. Rapid crosslinking of the droplets is obtained to form microspheres containing encapsulated cells.

By controlling the atomization conditions such as air and fluid flow rates the size of the microspheres may be controlled. The cell containing microspheres are cultured in tissue culture medium until such time as sufficient cell populations necessary for correction of the hepatic abnormality are deemed to have been produced. Thereafter, the microencapsulated cells are transplanted back into the liver.

The WSCP preferably is chosen to support cell adhesion or as a matrix that supports cell ingrowth (such as collagen or fibrin). The hydrogel is formed at the interface where the WSCP and the WSCA contact each other. It should be noted that a self condensible WSCA, such as an acrylated PEG (in the presence of or absence of a physically crosslinkable agent) also may be chosen to form a thin coating around the cell cluster or droplet. Methods for forming such coatings in the absence of a physical crosslinking agent are described in U.S. Pat. No. 5,529,914 to Hubbell et al., which is incorporated herein by reference.

Other cells that likewise may be encapsulated include:
(i) Neurotransmitter-Releasing Cells.

Paralysis agitans, more commonly called Parkinson's disease, is characterized by a lack of the neurotransmitter dopamine within the striatum of the brain. Dopamine secreting cells, such as cells from the ventral mesencephalon, from neuroblastoid cell lines or from the adrenal medulla may be encapsulated using the method and materials described herein. Cells, including genetically engineered cells, secreting a precursor for a neurotransmitter, an agonist, a derivative or a mimic of a particular neurotransmitter or analogs also may be encapsulated.

(ii) Encapsulation of Hemoglobin for Synthetic Erythrocytes

Hemoglobin in its free form may be encapsulated by a reactive inclusion at the time of forming hydrogels. This may be accomplished, for example, by selecting a WSCA that is amine or thiol reactive and by picking a WSCP which has these functional groups too. A solution of hemoglobin may be made in either or both of these precursor solutions. The solutions are selected so that the crosslinking takes a 10–15 seconds to complete. This provides adequate time to disperse the two solutions, pumped via a syringe pump through a static mixer and into an oil bath under vortexing or ultrasonication conditions to achieve dispersion of the solutions.

Microspheres are formed and the dispersal conditions are selected so that the resulting microspheres are of a certain desired size, for example, to mimic physiological erythrocytes. The crosslinking process then is allowed to proceed and the microspheres are separated by filtration, sedimentation or by solvent extraction. The diffusion of hemoglobin from the gels is expected to be low, due to covalent binding to the network. The entrapment of hemoglobin in small spheres of less than 5 microns in diameter of these highly biocompatible materials would lead to enhanced circulation times relative to crosslinked hemoglobin or liposome encapsulated hemoglobin.

Example 11
Embolization of Biopsy Needle Tracks

With increasing use of percutaneous biopsy greater experience and larger series have clarified some subtle points and controversies about possible complications and their prevention. While hemorrhage is possible with even the smallest aspiration needle, its risk has been assumed to increase significantly with the use of larger cutting needles and/or in patients with coagulation deficiencies. Thus, biopsy is considered a high-risk procedure in patients with low platelet counts, and is often deferred if the coagulopathy can be corrected.

Bleeding complications and leakage from other organs containing fluids, e.g., airleaks from lungs, may be minimized if the tracks left by the biopsy needles are injected with an embolization material that forms a hydrogel in situ and occludes the track. Thus, the composition and catheters similar to those described in Example 7 may be used for this purpose.

When a foamed gel is desired, a compound that effervesces upon exposure to an acidic pH or by other mechanisms may be incorporated in either the WSCA or the WSCP, so that the foaming gas is liberated when the tow components come into contact with each other and are in the process of polymerizing to form the hydrogel. The released gases can become entrapped by the forming gel, causing the formation of a stable foamed gel.

Example 12
Hydrogel Composition Formed using a Complexation Induced Physical Crosslinking and a Free Radical Polymerization for Chemical Crosslinking The first solution, or the WSCA solution, is prepared by dissolving an acrylated co-polymer of PEG (M.W. 8,000) and poly(d,l lactic acid) at a concentration of 15% w/w in phosphate buffered saline, which additionally contains 0.5% w/w ferrous gluconate to form the "WSCA solution". The WSCA in this case also serves as the WSCP due to the self crosslinking nature of the acrylate end groups. A second solution which consists of poly(acrylic acid) (PAA, M.W. 10,000 da) dissolved at a concentration of 15% w/w, and additionally containing 100 ppm of hydrogen peroxide, is prepared. The two solutions are sprayed onto the surface of surgically exposed peritoneal tissues in a rabbit model for postsurgical adhesion formation.

A spray type applicator, that has the ability to atomize the two solutions so that they mix only at the site of application, is used for the deposition. An almost immediate complexation and gelation will be evident due to the interaction of the PEG with the PAA due to the formation of physical crosslinks. Within 30 seconds the covalent crosslinking, which is initiated by a Fenton's type reaction between the iron and the hydrogen peroxide, causes the covalent crosslinking of the acrylated macromer to result in the formation of a physically resilient and tissue adherent hydrogel.

Example 13
Local Delivery of a Therapeutic Substance

The WSCA solution is prepared as described in Example 10 above and additionally 10 mg/ml of tissue plasminogen activator is dissolved to form a homogeneous solution. The second solution is prepared as described above. The hydrogel formed after co-spraying these two solutions now is capable of slowly releasing t-PA at the sites of surgery that are at risk for adhesion formation. Thus, the therapeutic effect is not only obtained by the presence of a hydrogel barrier but also by the local delivery of a pharmaceutical agent.

Any of a variety of therapeutic or diagnostic agents (including radiopharmaceuticals or radio-opacifiers) may be similarly included in the hydrogel formulations.

Example 14
Coating of Macro or Microencapsulating Devices

The hydrogel materials of the present invention may be applied to the treatment of device surfaces, such as those used for ultrafiltration, hemodialysis and non-microencapsulated immunoisolation of animal tissue. The macrocapsule in this case will usually be microporous with a molecular weight cutoff below 70,000 Da. It may be in the form of a hollow fiber, a spiral module, a flat sheet or other configuration. The surface of such a microcapsule may be modified using a WSCA and/or WSCP which predominantly contains PEG, which has known surface modification properties, to produce a non-fouling, non-thrombogenic, and non-cell-adhesive surface. The coating serves to enhance biocompatibility and to offer additional immunoprotection.

A variety of methods may be employed to form biocompatible overcoats, depending on the physical and chemical nature of the surface. Hydrophilic surfaces may be coated by applying a thin layer (for example, between 50 and 300 microns in thickness) of a polymerizable solution such as PEG diacrylate containing appropriate amounts polymerization initiators. Hydrophobic surfaces may be first rendered hydrophilic by gas plasma discharge treatment or by use of co-solvents. The resulting surface then may be similarly coated, or they may simply be treated with a surfactant before or during treatment with the PEG diacrylate solution.

For example, a hydrophobic polystyrene surface first may be treated by exposure to an oxygen or nitrogen plasma. This step renders the surface more hydrophilic by the creation of oxygen-containing or nitrogen containing surface species, respectively. These species may be further treated by reaction with a substance such as acryloyl chloride, capable of producing surface-bound free radical sensitive species. Alteratively, amine reactive WSCA species could be used to bind to the surface directly. A hydrophobic polystyrene surface also first may be treated with a surfactant, such as a poly(ethylene oxide)-poly(propylene oxide) block copolymer, which subsequently may be acrylated, if desired. Such treatments will enhance adhesion between the hydrophilic coating layers and the hydrophobic material being treated.

Example 15
Entrapment of Enzymes for Correction of Metabolic Disorders and Chemotherapy There are many diseases and defects that result from a deficiency in enzymes. For example, congenital deficiency of the enzyme catalase causes acatalasemia. Covalent immobilization of catalase in PEG gel networks provides a method of enzyme replacement to treat this disease. Entrapment of glucosidase similarly may be useful in treating Gaucher's disease. Microspherical PEG gels entrapping urease may be used in extracorporeal blood to convert urea into ammonia.

Enzymes such as asparaginase can degrade amino acids needed by tumor cells. Immunogenicity of these enzymes prevents direct use for chemotherapy. Entrapment of the foregoing enzyme, however, in PEG gels, may support successful chemotherapy. The enzyme may be reactively incorporated within the hydrogel network so as to have minimal or no release of the enzyme, while still allowing metabolically active species to diffuse in and out of the hydrogel.

Example 16
Coating of Tissues and Organs

Materials that may be advantageously modified include synthetic materials such as polysulfones, cellulosic membranes, polycarbonates, polyamides, polyimides, polybenzimidazoles, nylons, poly(acrylonitrile-co-vinyl chloride) copolymers, polyurethanes, polystyrene, poly (styrene co-acrylonitriles), poly(vinyl chloride), and poly (ethylene terephthalate). Natural materials, such as allogeneic, or xenogeneic tissues, e.g., heart valves, blood vessels, pericardial membranes, fascia lata, dura mater, etc., easily may be modified in this fashion since tissue is known to have amine, carboxyl and other reactive functional groups on its surface that react with appropriate WSCA species.

Accordingly, this approach may be used to reduce the immunogenecity of such tissues while still retaining the physical and mechanical properties of the native tissues. This approach also may be used for modifications of whole organs. For example, it is envisioned that an allogeneic liver, pancreas or heart may be perfused with a WSCA that reacts with the vasculature and renders it less immunogenic prior to transplantation.

While preferred illustrative embodiments of the invention are described above, it will be apparent to one skilled in the art that various changes and modifications may be made therein without departing from the invention, and it is intended in the appended claims to cover all such changes

What is claimed is:

1. A hydrogel system for forming a medical implant in situ in a human body, the hydrogel system comprising:
a first component that forms physical crosslinks to make a water-insoluble gel in situ immediately upon introduction into the human body, and
a second component that forms chemical crosslinks in situ,
wherein the physical crosslinks formed by the first component stabilize and confine the second component in situ during formation of the chemical crosslinks;
with the first component including a first polymer that is chosen from the group consisting of a thermoreversible polymer, a hydrophobic thermoreversible polymer, a pH responsive polymer, a composition of polymers with opposite ionic charges, a composition of a poly(alkylene) oxide plus a second polymer that undergoes an association reaction with the poly(alkylene) oxide, a thixotropic polymer, a polymer that gels upon cooling, and a polymer that forms physical crosslinks in response to a divalent cation;
with the second component including a second polymer that includes chemical groups for forming covalent bonds; and
the second component being a substantially water soluble macromer.

2. The hydrogel system of claim 1 wherein the second component forms chemical crosslight by a mechanism selected from a group consisting of free radical polymerization, condensation polymerization, anionic or cationic polymerization, and step growth polymerization.

3. The hydrogel system of clam 1 wherein the first component also forns chemical crosslinks by a mechanism selected ftom a group consisting of free radical polymerization, condensation polymerization, anionic or cationic polymerization, and step growth polymerization.

4. The hydrogel system of claim 1 wherein the macromer comprises a water soluble crosslinking agent.

5. The hydrogel system of claim 4 wherein the water soluble crosslinking agent is self condedsible.

6. The hydrogel system of claim 1 wherein the second component comprises a water soluble crosslinkable polymer.

7. The hydrogel system of claim 1 wherein the stability and reactivity of the first and second components is a function of the pHs of the first and second components.

8. The hydrogel system of claim 1 wherein the implant is biodegradable.

9. The hydrogel system of claim 1 wherein at least one of the components has the structure:

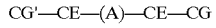

wherein,
(A) is a di or multifunctional substantially water soluble polymeric backbone;
CG and CG' are active crossing or leavring group portions; and
(—CE—) is an optional chain extending segment.

10. The hydrogel system of claim 9 wherein the reactive functional groups CG and CG' are different.

11. The hydrogel system of claim 9 wherein at least one optional chain extending segment CE is interposed between two chemical crosslinks and is degradable.

12. The hydrogel system of claim 11 wherein the chemical groups are chosen from the group consisting of chemical groups that undergo free radical polymerization, condensation polymerization, anionic polymerization, cationic polymerization, and step growth polymerization, or
chosen fom the group consisting of electrophilic and nucleophilic chemical groups.

13. A system for forming a medical implant in a human body in situ comprising:
a first comoponent and a second component that cooperate in situ; comprising:
the first component including a substantially water soluble precursor that forms a mechanically stable water-insoluble gel in situ stabilized by physical crosslinks;
with the first component being a first poloymer chosen from the group consisting of a themoreversible polymer, a hydrophobic thermoreversible polymer, a pH responsive polymer, a composition of polymers with opposite ionic charges, a composition of a poly(alkylene) oxide and a polymer that undergoes an association reaction with the poly(alkylene) oxide, a thixotropic polymer, a polymer that gels upon cooling, and a polymer that forms physical crosslinks in response to a divalent cation;
with the second component being a second polymer including chemical groups for forming covalent bonds wherein the chemical groups include N-hydroxy succinamide esters.

14. The system of claim 13 wherein the chemical groups are chosen from the group consisting of chemical groups that undergo free radical polymerization, condensation polymerization anionic polymerization, cationic polymerization, and step growth polymerization.

15. The system of claim 13 wherein the chemical groups are chosen from the group consisting of electrophilic and nucleophilic chemical groups.

16. The system of claim 13 wherein the first component is a thermoreversible polymer.

17. The system of claim 13 wherein the first component comprises poly(oxyethylene)-poly(oxypropylene) block copolymer and the second component comprises N-hydroxy succinamide ester on the second polymer that is covalently linkable by the N-hydroxy succinamide ester to a third polymer having at least one nucleophilic group.

18. The system of claim 13 further comprising at least one color indicator substance.

19. The system of claim 18 wherein the color indicator substance is chosen from the group consisting of phenol red, thymol blue, furoxone, rivanol, or picric acid.

20. The system of claim 18 wherein the color indicator substance is blue, yellow, or green.

21. The system of claim 18 wherein the color indicator substance is a first color when the system is stored and a second color when the system is disposed in situ.

22. A hydrogel system for forming a medical implant in situ in a human body, the hydrogel system comprising:
a first component comprising a polymer that is chosen from the group consisting of a thermoreversible polymer and a polymer that forms physical crosslinks in response to a divalent cation; and
a second component that forms chemical crosslinks in situ, with the second component being a substantially water soluble macromer and comprising N-hydroxy succinamide ester chemical groups for forming covalent bonds with nucleophiles.

23. The hydrogel system of claim 22 wherein the implant is biodegradable.

24. The hydrogel system of claim 22 wherein at least one of the components has the structure:

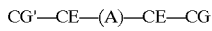

wherein,
(A) is a di or multifunctional substantially water soluble polymeric backbone;
CG and CG' are active crosslinking or leaving group portions; and
(—CE—) is an optional chain extending segment.

25. The hydrogel system of claim 22 wherein the reactive functional groups CG and CG' are different.

26. The hydrogel system of claim 22 wherein at least one optional chain extending segment CE is interposed between two chemical crosslinks and is degradable.

27. The system of claim 22 wherein the first component is a thermoreversible polymer.

28. The system of claim 22 wherein the first component comprises poly(oxyethylene)-poly(oxypropylene) block copolymer and the second component comprises N-hydroxy succinamide ester on the second polymer that is covalently linkable by the N-hydroxy succinamide ester to a third polymer having at least one nucleophilic group.

29. The system of claim 22 further comprising at least one color indicator substance.

30. The system of claim 29 wherein the color indicator substance is chosen from the group consisting of phenol red, thymol blue, furoxone, rivanol, or picric acid.

31. The system of claim 29 wherein the color indicator substance is blue, yellow, or green.

32. The system of claim 29 wherein the color indicator substance is a first color when the system is stored and a second color when the system is disposed in situ.

* * * * *